US012778432B2

(12) United States Patent
Cao et al.

(10) Patent No.: US 12,778,432 B2
(45) Date of Patent: Nov. 3, 2026

(54) VIDEO DATA-BASED SYSTEM FOR BLOOD PRESSURE PREDICTION

(71) Applicant: Lepu Medical Technology (Beijing) Co., Ltd, Beijing (CN)

(72) Inventors: Jun Cao, Beijing (CN); Zejian Wu, Beijing (CN); Sihan Wang, Beijing (CN); Biying Zhang, Beijing (CN); Hongdai Sun, Beijing (CN); Zhe Li, Beijing (CN); Chengzhong Zhang, Beijing (CN); Ruilai Li, Beijing (CN); Kaifeng Zang, Beijing (CN); Ruiguang Lu, Beijing (CN); Yuelei Wang, Beijing (CN); Liang Ban, Beijing (CN); Xiaole Zhao, Beijing (CN); Xin Qi, Beijing (CN)

(73) Assignee: Lepu Medical Technology (Beijing) Co., Ltd, Changping (CN)

(*) Notice: Subject to any disclaimer, the term of this patent is extended or adjusted under 35 U.S.C. 154(b) by 701 days.

(21) Appl. No.: 18/248,713

(22) PCT Filed: Apr. 19, 2021

(86) PCT No.: PCT/CN2021/088017

§ 371 (c)(1),
(2) Date: Apr. 12, 2023

(87) PCT Pub. No.: WO2022/077887

PCT Pub. Date: Apr. 21, 2022

(65) Prior Publication Data

US 2023/0389808 A1 Dec. 7, 2023

(30) Foreign Application Priority Data

Oct. 12, 2020 (CN) ........................ 202011086786.5

(51) Int. Cl.
*A61B 5/021* (2006.01)
*A61B 5/00* (2006.01)
(Continued)

(52) U.S. Cl.
CPC ............ *A61B 5/021* (2013.01); *A61B 5/0059* (2013.01); *A61B 5/02416* (2013.01); *A61B 5/725* (2013.01); *H04L 9/3213* (2013.01)

(58) Field of Classification Search
CPC ... A61B 5/021; A61B 5/0059; A61B 5/02416; A61B 5/725; A61B 5/1032;
(Continued)

(56) References Cited

U.S. PATENT DOCUMENTS

2016/0242700 A1* 8/2016 Ferber .................. A61B 5/7239
2017/0238805 A1* 8/2017 Addison .............. A61B 5/1032
(Continued)

FOREIGN PATENT DOCUMENTS

CN 106343989 A 1/2017
CN 107049281 A 8/2017
(Continued)

OTHER PUBLICATIONS

International Search Report for International Application No. PCT/CN2021/088017 dated Jul. 23, 2021, 3 pages.
(Continued)

*Primary Examiner* — Tse Chen
*Assistant Examiner* — Evelyn Grace Park
(74) *Attorney, Agent, or Firm* — TraskBritt

(57) ABSTRACT

A video data-based system for blood pressure prediction. The video data-based system for blood pressure prediction comprises: a first device and a cloud server, where the first device comprises a first master control module, a first camera, a lighting module, a display screen, and a first communication; the cloud server comprises a second master
(Continued)

control module, a validity validation module, a parameter validation module, a data preprocessing module, an artificial intelligence blood pressure prediction module, and a second communication module. The use of the video data-based system for blood pressure prediction provided in the embodiments of the present disclosure obviates the need to wear any specific collecting device for the real-time detection and continuous monitoring of the blood pressure, thus reducing the difficulty of implementing the real-time detection and monitoring of a test subject, and enriching the application scenarios of photoplethysmography in the field of guardianship.

8 Claims, 1 Drawing Sheet

(51) Int. Cl.
*A61B 5/024* (2006.01)
*H04L 9/32* (2006.01)

(58) Field of Classification Search
CPC ... A61B 5/7225; A61B 5/0077; A61B 5/7203; A61B 5/7257; A61B 5/726; A61B 5/0022; A61B 5/02116; A61B 5/6898; A61B 5/7267; A61B 5/02; H04L 9/3213; H04L 67/12; H04L 2209/88; H04L 12/4633; H04L 63/123; H04L 67/02; H04L 67/565; G16H 30/40; G16H 40/67; G16H 50/20
See application file for complete search history.

(56) References Cited

U.S. PATENT DOCUMENTS

2018/0199870 A1 7/2018 Lee et al.
2018/0295134 A1 10/2018 Gupta et al.
2018/0303351 A1 10/2018 Mestha et al.
2019/0313907 A1 10/2019 Khachaturian et al.
2020/0196881 A1* 6/2020 Zemel ................ A61B 5/02444
2020/0260956 A1* 8/2020 Lee ...................... A61B 5/0077

FOREIGN PATENT DOCUMENTS

CN 108234122 A 6/2018
CN 109009034 A 12/2018
CN 110251105 A 9/2019
CN 111179454 A 5/2020
CN 111297339 A 6/2020
CN 111297347 A 6/2020
CN 111358455 A 7/2020
CN 112315437 A 2/2021
EP 3705032 A1 9/2020

OTHER PUBLICATIONS

International Written Opinion for International Application No. PCT/CN2021/088017 dated Jul. 23, 2021, 3 pages.
Chinese Search Report for Chinese Application No. 202011086786.5, dated Feb. 29, 2024, 1 pages.
First Office Action for Chinese Application No. 202011086786.5, dated Feb. 29, 2024, 16 pages with English translation.
Notification to Grant Patent Right for Invention for Chinese Application No. 202011086786, dated Jul. 12, 2024, 3 pages with English translation.
European Extended Search Report and Opinion for European Application No. 21878941.0, dated Sep. 25, 2024, 11 pages.
European Communication pursuant to Article 94(3) EPC for European Application No. 21878941.0, dated Mar. 25, 2026, 5 pages.

* cited by examiner

VIDEO DATA-BASED SYSTEM FOR BLOOD PRESSURE PREDICTION

CROSS-REFERENCE TO RELATED APPLICATIONS

This application is a national phase entry under 35 U.S.C. § 371 of International Patent Application PCT/CN2021/088017, filed Apr. 19, 2021, designating the United States of America and published as International Patent Publication WO 2022/077887A1 on Apr. 21, 2022, which claims the benefit under Article 8 of the Patent Cooperation Treaty to Chinese Patent Application Serial No. 202011086786.5, filed Oct. 12, 2020.

TECHNICAL FIELD

The present disclosure relates to the technical field of signal processing, particularly to a video data-based system for a blood pressure prediction.

BACKGROUND

Photoplethysmography is a non-invasive detection method for detecting a volume change of a blood in a viable tissue by means of an optoelectronic technique. Blood flow volume of unit area in a blood vessel will change periodically due to cardiac impulse, and the corresponding blood volume will change correspondingly, so that a photoplethysmography signal reflecting the quantity of light absorbed by blood will change periodically, too. Periodical change of a conventional photoplethysmography signal is closely related to cardiac impulse and blood pressure change. Inter-beat interval analysis on the conventional photoplethysmography signal is performed to obtain heart beat data of a heart. Blood pressure related analysis on the conventional photoplethysmography signal is performed by using a well-trained artificial intelligence blood pressure prediction model, so as to obtain diastolic pressure and systolic pressure data of blood pressure. A remote photoplethysmography signal is a periodical signal generated as skin absorbs or reflects light. A method for calculating heart beat and analyzing blood pressure based on the remote photoplethysmography signal is the same as a method based on the photoplethysmography signal. However, a test object needs to wear customized collecting devices (for example, collecting devices such as finger clips and ear clips) to collect the conventional photoplethysmography signal, which is not only inconvenient for the test object to perform own point-of-care detection, but also inconvenient to monitor the test object persistently. It is only needed to shoot a skin surface by a high definition camera and further perform optical channel data conversion on video data to obtain the remote photoplethysmography signal.

BRIEF SUMMARY

The objective of the present disclosure is to provide a video data-based system for a blood pressure prediction by overcoming defects in the prior art. The system includes a first device and a cloud server. The blood pressure can be detected in real time and monitored persistently by using the system without wearing any specific collecting device, thereby not only reducing the implementation difficulty to detect the blood pressure of a test object in real time and monitoring the blood pressure thereof persistently, but also enriching the application scenes of photoplethysmography in the monitoring field.

In order to achieve the abovementioned objective, the present disclosure provides a video data based system for a blood pressure prediction, including a first device and a cloud server,

- where the first device includes a first master control module, a first camera, a light module, a display screen and a first communication module;
- the first master control module is configured to call the first camera and the light module to perform shooting processing on an epidermal area of a test object for a first duration, so as to generate first video data;
- the display screen is configured to receive the first video data sent by the master control module to perform play processing;
- the first master control module is further configured to perform extraction processing of light source channel data on the first video data according to light source information so as to generate first channel data; then performing remote photoplethysmography signal data conversion processing on the first channel data to generate first signal data; and then sending the first signal data to the display screen to perform signal waveform display processing according to a display duration;
- the first master control module is further configured to encapsulate the first signal data, first device token information, first device type information, and first age information, first gender information, first height information and first weight information of the test object to a first data packet according to a first protocol, and send the first data packet to the cloud server by means of the first communication module;
- the cloud server includes a second master control module, a validity verification module, a parameter verification module, a data pre-processing module, an artificial intelligence blood pressure prediction module and a second communication module;
- the second master control module is configured to perform data analysis processing on the first data packet according to the first protocol, so as to obtain second signal data, second device token information, second device type information, second age information, second gender information, second height information and second weight information;
- the validity verification module is configured to perform validity verification processing on the second device token information according to a valid token list;
- the parameter verification module is configured to, when the validity verification processing is successful, perform parameter verification processing on the second signal data, the second device token information, the second device type information, the second age information, the second gender information, the second height information and the second weight information;
- the second master control module is further configured to, when the parameter integrity verification processing is successful, perform heart rate calculation processing according to the second signal data, so as to generate heart rate data;
- the data pre-processing module is configured to perform input data preparation processing of a blood pressure prediction module on the second signal data, the second age information, the second gender information, the second height information and the second weight information according to identifier information of the prediction module, so as to generate input data of the model;

the artificial intelligence blood pressure prediction module is configured to perform blood pressure prediction operation processing on the input data of the model according to the identifier information of the prediction module, so as to generate diastolic pressure data and systolic pressure data;

the second master control module is further configured to set state code data to be normal state code information, then constitute return data according to the heart rate data, the diastolic pressure data and the systolic pressure data, then encapsulate the return data and the state code data to a second data packet according to the first protocol, and send the second data packet to the first device by means of the second communication module; and the first master control module is further configured to perform data analysis processing on the second data packet according to the first protocol, so as to obtain the return data and the state code date; acquire, when the state code data is the normal state code information, the heart rate data, the diastolic pressure data and the systolic pressure data from the return data; and then send the heart rate data, the diastolic pressure data and the systolic pressure data to the display screen to perform heart rate and blood pressure data display processing.

Preferably, the first master control module is specifically configured to call the light module to irradiate the epidermal area of the test object and perform shooting processing on the epidermal area for the first duration after a lens of the first camera covers the epidermal area, so as to generate first video data.

Preferably, the first master control module is specifically configured to, when the light source information is red light, perform red light channel data extraction processing on the first video data, so as to generate the first channel data; when the light source information is green light, perform green light channel data extraction processing on the first video data, so as to generate first channel data; when the light source information is red and green light, perform red light channel data extraction processing on the first video data, so as to generate first red light channel data, perform green light channel data extraction processing on the first video data, so as to generate first green light channel data, and encapsulate the first red light channel data and the first green light channel data to the first channel data.

Preferably, the first master control module is specifically configured to, when the light source information is red light, perform frame image extraction processing on the first video data, so as to obtain a plurality of first frame image data; count a quantity of first red pixel points with a pixel value meeting a red light pixel threshold range in each of the first frame image data, so as to generate a first aggregate, and perform summation calculation on the pixel values of all the first red pixel points, so as to generate a first pixel value sum, and then take a ratio of the first pixel value sum to the first aggregate as first frame red light channel data corresponding to each of the first frame image data; and then rank all the first frame red light channel data in a chronological order, so as to generate the first channel data;

the first master control module is specifically configured to, when the light source information is green light, perform frame image extraction processing on the first video data, so as to obtain a plurality of second frame image data; count a quantity of first green pixel points with a pixel value meeting a green light pixel threshold range in each of the second frame image data, so as to generate a second aggregate, and perform summation calculation on the pixel values of all the first green pixel points, so as to generate a second pixel value sum, and then take a ratio of the second pixel value sum to the second aggregate as first frame green light channel data corresponding to each of the second frame image data; and then rank all the first frame green light channel data in a chronological order, so as to generate the first channel data; and the first master control module is specifically configured to, when the light source information is red and green light, perform frame image extraction processing on the first video data, so as to obtain a plurality of third frame image data; count a quantity of second red pixel points with a pixel value meeting a red light pixel threshold range in each of the third frame image data, so as to generate a third aggregate, and perform summation calculation on the pixel values of all the second red pixel points, so as to generate a third pixel value sum, and then take a ratio of the third pixel value sum to the third aggregate as second frame red light channel data corresponding to each of the third frame image data, and then rank all the second frame red light channel data in a chronological order, so as to generate the first red light channel data; count a quantity of second green pixel points with a pixel value meeting a green light pixel threshold range in each of the third frame image data, so as to generate a fourth aggregate, and perform summation calculation on the pixel values of all the second green pixel points, so as to generate a fourth pixel value sum, and then take a ratio of the fourth pixel value sum to the fourth aggregate as second frame green light channel data corresponding to each of the third frame image data, and then rank all the second frame green light channel data in a chronological order, so as to generate the first green light channel data; and then perform multi-channel data encapsulation processing on the first red light channel data and the first green light channel data, so as to generate the first channel data.

Preferably, the first master control module is specifically configured to, when the light source information is the red light, perform remote photoplethysmography signal band-pass filtering processing on the first channel data, so as to generate first red light filter data, and then perform remote photoplethysmography signal denoise processing on the first red light filter data, so as to generate first red light signal data;

the first master control module is specifically configured to, when the light source information is the green light, perform remote photoplethysmography signal band-pass filtering processing on the first channel data, so as to generate first green light filter data, and then perform remote photoplethysmography signal denoise processing on the first green light filter data, so as to generate first green light signal data; and the first master control module is specifically configured to, when the light source information is the red and green light, perform red light channel data extraction processing on the first channel data, so as to generate second red light channel data, and perform green light channel data extraction processing on the first channel data, so as to generate second green light channel data; then respectively perform remote photoplethysmography signal band-pass filtering processing on the second red light channel data and the second green light channel data, so as to generate second red light filter data and second green light filter data; and then respectively perform remote photoplethysmography signal denoise processing on the second red light filter data and the second green light filter data, so as to generate second red light signal data and second green light signal data.

Preferably, the first master control module is specifically configured to, when the light source information is the red light, intercept the latest data segment with a duration being the display duration from the first red light signal data, so as to generate first red light display data; then perform waveform image data conversion processing on the first red light display data, so as to generate first red light waveform image data; and then send the first red light waveform image data to the display screen to perform first red light waveform display processing;

the first master control module is specifically configured to, when the light source information is the green light, intercept the latest data segment with a duration being the display duration from the first green light signal data, so as to generate first green light display data; then perform waveform image data conversion processing on the first green light display data, so as to generate first green light waveform image data; and then send the first green light waveform image data to the display screen to perform first green light waveform display processing;

the first master control module is specifically configured to, when the light source information is the red and green light, intercept the latest data segment with a duration being the display duration from the second red light signal data, so as to generate second red light display data, then perform waveform image data conversion processing on the second red light display data, so as to generate second red light waveform image data; intercept the latest data segment with a duration being the display duration from the second green light signal data, so as to generate second green light display data, then perform waveform image data conversion processing on the second green light display data, so as to generate second green light waveform image data; and then send the second red light waveform image data to the display screen to perform second red light waveform display processing and send the second green light waveform image data to the display screen to perform second green light waveform display processing.

Preferably, the first protocol includes a Hyper Text Transfer Protocol (HTTP) and a Hyper Text Transfer Protocol over Secure Socket Layer (HTTPS);

the second signal data is equivalent to the first signal data, the second device token information is equivalent to the first device token information, the second device type information is equivalent to the first device type information, the second age information is equivalent to the first age information, the second gender information is equivalent to the first gender information; the second height information is equivalent to the first height information, and the second weight information is equivalent to the first weight information;

the first communication module is specifically configured to be accessed to the Internet via a mobile communication network, a wireless local area network or a wired local area network; and the second communication module is specifically configured to be accessed to the Internet via a mobile communication network, a wireless local area network or a wired local area network.

Preferably, the validity verification module is specifically configured to inquire the valid token list according to the second device token information, and when the second device token information satisfies the valid token list, the validity verification processing is successful.

Preferably, the parameter verification module is specifically configured to examine whether none of the second signal data, the second device type information, the second age information, the second gender information, the second height information and the second weight information is null, and when none of the second signal data, the second device type information, the second age information, the second gender information, the second height information and the second weight information is null, the parameter verification processing is successful.

Preferably, the data pre-processing module includes a plurality of sub pre-processing modules, and the artificial intelligence blood pressure prediction module comprises a plurality of sub blood pressure prediction modules;

the data pre-processing module is specifically configured to select the corresponding first sub pre-processing module to perform input data preparation processing of the first sub blood pressure prediction module on the second signal data, the second age information, the second gender information, the second height information and the second weight information according to identifier information of the prediction module, so as to generate input data of a first model;

the first sub pre-processing module is specifically configured to baseline drift elimination processing on the second signal data, so as to generate first process signal data, then perform denoise processing on the first process signal data, so as to generate second process signal data, and then perform standard sampling and normalization processing on the second process signal data, so as to generate standard signal data; and then encapsulate the second signal data, the second age information, the second gender information, the second height information, the second weight information and the standard signal data to the input data of the first model according to an input data format requirement of the first sub blood pressure prediction module; and the artificial intelligence blood pressure prediction module is specifically configured to select the corresponding first sub blood pressure prediction module to perform first blood pressure prediction calculation processing on the input data of the first model according to the identifier information of the prediction module, so as to generate diastolic pressure data and systolic pressure data.

A video data based system for a blood pressure prediction provided by the embodiment of the present disclosure includes a first device and a cloud server, where the first device performs video shooting on an epidermal area of a test object by using a first camera to obtain first video data, and then performs remote photoplethysmography signal conversion processing on the first video data to obtain first signal data. The cloud server then performs heart beat analysis on the first signal data to obtain heart beat data, and performs blood pressure analysis on the input data of the model integrating personalized data (information such as age, gender, height and weight) and the first signal data by using the artificial intelligence blood pressure prediction model to obtain blood pressure data (systolic pressure and diastolic pressure). Finally, the cloud server returns the analyzed data (heart beat data, systolic pressure data and diastolic pressure data) to the first device to be displayed. The test object can be detected in real time or monitored persistently by using the system without wearing any specific collecting device, thereby reducing the implementation difficulty to detect the blood pressure of the test object in real time and monitoring the blood pressure thereof persistently and enriching the application scenes of photoplethysmography in the monitoring field.

DETAILED DESCRIPTION

In order to make objectives, technical solutions and advantages of the present disclosure clearer, further description will be made on the present disclosure below in combination with the accompanying drawings. It is apparent that the described embodiments are merely a part of embodiments of the present disclosure and are not all the embodiments. On a basis of the embodiments in the present disclosure, all other embodiments obtained by those of ordinary skill in the art without creative efforts fall into the scope of protection of the present disclosure.

A video data-based system for a blood pressure prediction provided by an embodiment of the present disclosure includes a first device and a cloud server, where the first device includes a first master control module, a first camera, a display screen and a first communication module. The cloud server includes a second master control module, a validity verification module, a parameter verification module, a data pre-processing module, an artificial intelligence blood pressure prediction module and a second communication module.

The first device herein may be a terminal device, a computer, a notebook computer, a mobile phone, a tablet personal computer, a mobile terminal or a server, etc., and capable of being accessed to the Internet by way of a mobile communication network, a local area network (wired or wireless access way) or a wide area network (wired or wireless access way). The cloud server herein may be a terminal device, an independent server, a virtual server or a cloud architecture-based server capable of being accessed to the Internet by way of a mobile communication network, a local area network (wired or wireless access way) or a wide area network (wired or wireless access way).

In a video data based system for a blood pressure prediction provided by the embodiment of the present disclosure, the first device performs video shooting on the epidermal area of the test object by using the first camera to obtain first video data, and then performs remote photoplethysmography signal conversion processing on the first video data to obtain first signal data. The cloud server then performs heart beat analysis on the first signal data to obtain heart beat data, and performs blood pressure analysis on the input data of the model integrating personalized data (information such as age, gender, height and weight) and the first signal data by using the artificial intelligence blood pressure prediction model to obtain blood pressure data (systolic pressure and diastolic pressure). Finally, the cloud server returns the analyzed data (heart beat data, systolic pressure data and diastolic pressure data) to the first device to be displayed.

Figure 1:
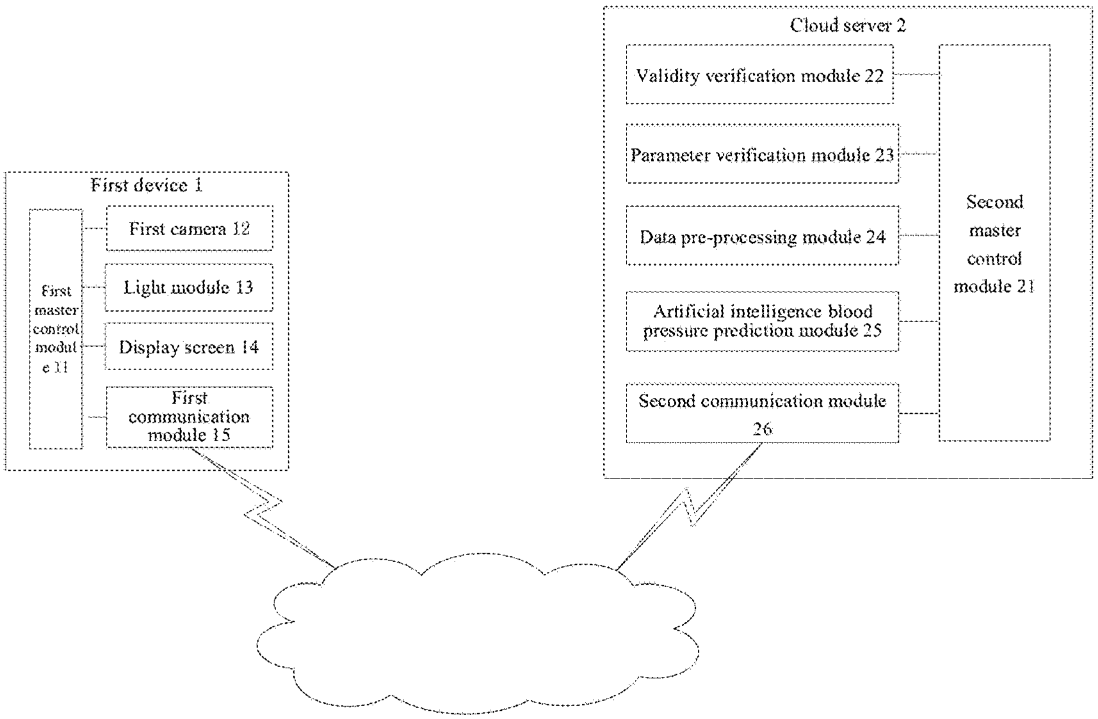
FIG. 1 is a video data-based system for a blood pressure prediction provided by an embodiment of the present disclosure.

FIG. 1 is a schematic diagram of a video data-based system for a blood pressure prediction provided by an embodiment of the present disclosure. As shown in FIG. 1, the system for predicting a blood pressure based on video data provided by an embodiment of the present disclosure includes a first device 1 and a cloud server 2.

The first device 1 includes a first master control module 11, a first camera 12, a light module 13, a display screen 14 and a first communication module 15.

For example, if the first device 1 is specifically a mobile phone, the first master control module 11 is then a control unit of the mobile phone, the first camera 12 is a main camera of the mobile phone, the light module 13 is a flashlight of the mobile phone, the display screen 14 is a screen of the mobile phone, and the first communication module 15 is a communication unit of the mobile phone.

The first master control module 11 is configured to call the first camera 12 and the light module 13 to perform shooting processing on an epidermal area of a test object for a first duration, so as to generate a first video data.

Herein, the epidermal area is a preset skin area of the test object, and the first duration is a preset shooting duration.

In a specific implementation mode provided by the embodiment, the first master control module 11 is specifically configured to call the light module 13 to irradiate the epidermal area of the test object and perform shooting processing on the epidermal area for the first duration by mans of the first camera 12 after a lens of the first camera 12 covers the epidermal area, so as to generate the first video data.

Figure 2:
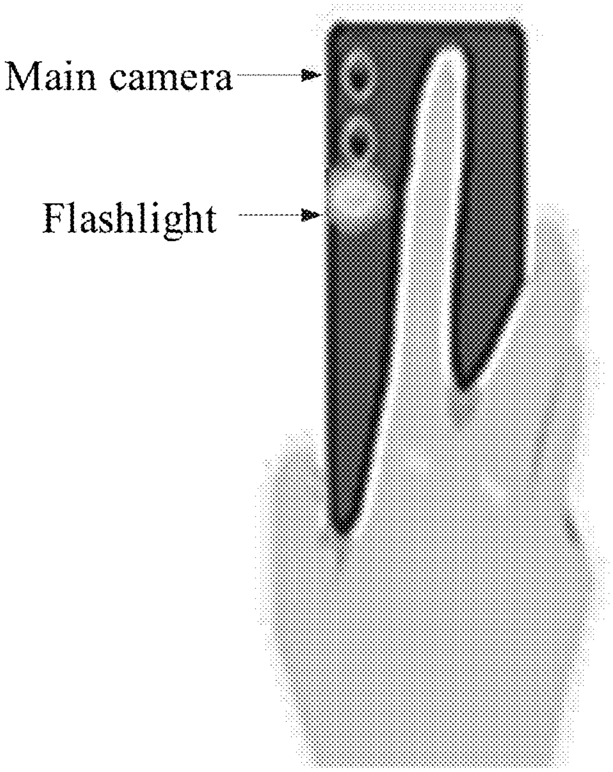
FIG. 2 is a schematic diagram of a shooting method provided by an embodiment of the present disclosure.

For example, when the epidermal area is a fingertip skin area, and the first duration is 26 seconds, as shown in FIG. 2, which is a schematic diagram of a shooting method provided by the embodiment of the present disclosure, the test object then irradiates fingertip skin by using the flashlight, and covers the fingertip skin totally with the main camera. The control unit of the mobile phone shoots the fingertip skin by using the main camera to obtain first video data with a duration being 26 seconds.

The display screen 14 is configured to receive the first video data sent by the master control module to perform play processing.

For example, in a 26-second shooting process, the display screen will play the first video data being shot in real time. In a normal condition, the test object shall attach the main camera in close proximity to the fingertip skin, and therefore, a first video picture being displayed is all-red.

The first master control module 11 is further configured to perform extraction processing of light source channel data on the first video data according to light source information so as to generate first channel data; then performing remote photoplethysmography signal data conversion processing on the first channel data to generate first signal data; and then sending the first signal data to the display screen 14 to perform signal waveform display processing according to a display duration.

Herein, the light source information includes red light, green light and red and green light.

Herein, the conventional photoplethysmography signal can only be collected under a red light or an infrared light source condition. The embodiment of the present disclosure supports shooting in a common light source environment (for example, a daylight environment), which not only supports recognition of a red light signal converted into the remote photoplethysmography signal and recognition of a green light signal converted into the remote photoplethysmography signal, but also supports recognition of the red and green light signal as well.

In another implementation mode provided by the embodiment, the first master control module 11 is specifically configured to, when the light source information is red light, perform red light channel data extraction processing on the first video data, so as to generate the first channel data; when the light source information is green light, perform green light channel data extraction processing on the first video data, so as to generate first channel data; when the light source information is red and green light, perform red light channel data extraction processing on the first video data, so as to generate first red light channel data, perform green light channel data extraction processing on the first video data, so as to generate first green light channel data, and encapsulate the first red light channel data and the first green light channel data to the first channel data.

Herein, the first master control module 11 is specifically configured to, when the light source information is red light, perform extraction processing of red light channel data on the first video data, so as to generate first channel data, the specific implementation mode as follows:

the first master control module 11 is specifically configured to, when the light source information is red light, perform frame image extraction processing on the first video data, so as to obtain a plurality of first frame image data; count a quantity of first red pixel points with a pixel value meeting a red light pixel threshold range in each of the first frame image data, so as to generate a first aggregate, and perform summation calculation on the pixel values of all the first red pixel points, so as to generate a first pixel value sum, and then take a ratio of the first pixel value sum to the first aggregate as first frame red light channel data corresponding to each of the first frame image data; and then rank all the first frame red light channel data in a chronological order, so as to generate the first channel data.

Herein, each first image frame is a two-dimensional bitmap consisting of a plurality of pixel points internally, each pixel point has a corresponding pixel value, and the first image data is a pixel value set of all pixel points in the first frame image. A red light pixel threshold range is a pixel value range, and the pixel points with the pixel values in accordance with the range are recognized as red pixel points.

For example, 24 frame images may be extracted from 1 second video data, and 26*24=624 first frame image data may be extracted from the first video data with a duration of 26 seconds. In the $1^{st}$ first frame image data, the amount of the first red pixel points is a first aggregate $N_R$, the sum of the pixel values of all the first red pixel points is a first pixel point sum $S_R$, and then the $1^{st}$ first frame red light channel data $C_R=S_R/N_R$. If the frame red light channel data herein must be an integer, it is needed to round the frame red light channel data. By reasoning from analogy in succession, 624 first frame red light channel data is obtained finally, and the first frame red light channel data is ranked in a chronological order to obtain the first channel data $\{C_{R1}, C_{R2} \ldots C_{R624}\}$.

Herein, when the light source information is a green light, extraction processing of green light channel data is performed on the first video data, so as to generate a first channel data, the specific implementation mode as follows:

the first master control module 11 is configured to, when the light source information is a green light, perform frame image extraction processing on the first video data, so as to obtain a plurality of second frame image data; count a quantity of second green pixel points with a pixel value meeting a green light pixel threshold range in each of the second frame image data, so as to generate a second aggregate, and perform summation calculation on the pixel values of all the second red pixel points, so as to generate a second pixel value sum, and then take a ratio of the second pixel value sum to the second aggregate as first frame green light channel data corresponding to each of the second frame image data; and then rank all the first frame green light channel data in a chronological order, so as to generate the first channel data.

Herein, each second image frame is a two-dimensional bitmap consisting of a plurality of pixel points internally, each pixel point has a corresponding pixel value, and the second image data is a pixel value set of all pixel points in the second frame image. A green light pixel threshold range is a pixel value range, and the pixel points with the pixel values in accordance with the range are recognized as green pixel points.

For example, 24 frame images can be extracted from 1 second video data, and 26*24=624 second frame image data can be extracted from the first video data with a duration of 26 seconds. In the first second frame image data, the amount of the first green pixel points is a second aggregate $N_G$, the sum of the pixel values of all the green pixel points is a second pixel point sum $S_G$, and then the $1^{st}$ first frame green light channel data $C_G=S_G/N_G$. If the frame green light channel data herein must be an integer, it is needed to round the frame green light channel data. By reasoning from analogy in succession, 624 first frame green light channel data is obtained finally, and the first frame green light channel data is ranked in a chronological order to obtain the first channel data $\{C_{G1}, C_{G2} \ldots C_{G624}\}$.

Herein, when the light source information is red and green light, red light channel data extraction processing is performed on the first video data, so as to generate first red light channel data, and green light channel data extraction processing is performed on the first video data, so as to generate a first green light channel data, and the first red light channel data and the first green light channel data are encapsulated to be the first channel data, the specific implementation mode as follows:

the first master control module 11 is configured to, when the light source information is a red and green light, perform frame image extraction processing on the first video data, so as to obtain a plurality of third frame image data; count a quantity of second red pixel points with a pixel value meeting a red light pixel threshold range in each of the third frame image data, so as to generate a third aggregate, and perform summation calculation on the pixel values of all the second red pixel points, so as to generate a third pixel value sum, and then take a ratio of the third pixel value sum to the third aggregate as second frame red light channel data corresponding to each of the third frame image data, and then rank all the second frame red light channel data in a chronological order, so as to generate the first red light channel data; count a quantity of second green pixel points with a pixel value meeting a green light pixel threshold range in each of the third frame image data, so as to generate a fourth aggregate, and perform summation calculation on the pixel values of all the second green pixel points, so as to generate a fourth pixel value sum, and then take a ratio of the fourth pixel value sum to the fourth aggregate as second frame green light channel data corresponding to each of the third frame image data, and then rank all the second frame green light channel data in a chronological order, so as to generate the first green light channel data; and then perform multi-channel data encapsulation processing on the first red light channel data and the first green light channel data, so as to generate the first channel data.

For example, 24 frame images can be extracted from 1 second video data, and 26*24=624 third frame image data can be extracted from the first video data with a duration of 26 seconds. In the first third frame image data, the quantity of the second red pixel points is a third aggregate $N'_R$, the quantity of the second green pixel points is a fourth aggregate $N'_G$, the sum of the pixel values of all the second red pixel points is a third pixel point sum $S'_R$, and the sum of the pixel values of all the second green pixel points is a fourth pixel point sum $S'_G$, and then the first second frame red light channel data $C'_R=S'_R/N'_R$. By reasoning from analogy in succession, the first red light channel data is $\{C'_{R1}, C'_{R2} \ldots C'_{R624}\}$, and the first second frame green light channel data is $C'_G=S'_G/N'_G$; by reasoning from analogy in succession, the first green light channel data is $\{C'_{G1}, C'_{G2} \ldots C'_{G624}\}$; and finally, the first channel data includes two groups of one-dimensional data: the first red light channel data and the first green light channel data.

In another implementation mode provided by the embodiment, the first master control module 11 is configured to, when the light source information is the red light, perform remote photoplethysmography signal band-pass filtering processing on the first channel data, so as to generate first red light filter data, and then perform remote photoplethysmography signal denoise processing on the first red light filter data, so as to generate first red light signal data.

For example, when the light source information is red, the first channel data consists of the red light channel data, the control unit of the mobile phone is preset with a threshold range of filtering frequency of remote photoplethysmography signal band-pass, the control unit then regards the first channel data as a segment of signal data and calculates signal frequency of each signal data point in the first channel data, and further, based on a band-pass filtering principle, deletes the red light channel data corresponding to the signal data with the signal frequency lower than or higher than the frequency threshold range in the first channel data, so as to obtain first red light filter data. Herein, the band-pass filtering frequency threshold range is usually 0.5-10 Hz. When band-pass filtering processing is performed on some mobile phones, in consideration of limited processing capacities the mobile phones, a finite impulse response (FIR) filter module may be used herein. The process of remote photoplethysmography signal denoise processing on the first red light filter data is approximate to the band-pass filtering processing process, which may be regarded as secondary filtering. The first signal data, which is the first red light signal data is finally obtained.

In another implementation mode provided by the embodiment, the first master control module 11 is configured to, when the light source information is the green light, perform remote photoplethysmography signal band-pass filtering processing on the first channel data, so as to generate first green light filter data, and then perform remote photoplethysmography signal denoise processing on the first green light filter data, so as to generate first green light signal data.

For example, when the light source information is green, the first channel data consists of the green light channel data, the control unit of the mobile phone regards the first channel data as a segment of signal data and calculates signal frequency of each signal data point in the first channel data, and further, based on a band-pass filtering principle, deletes the green light channel data corresponding to the signal data with the signal frequency lower than or higher than the frequency threshold range in the first channel data, so as to obtain first green light filter data. Then remote photoplethysmography signal denoise processing is performed on the first red light filter data to finally obtain the first signal data, which is the first green light signal data.

In another specific implementation mode provided by the embodiment, the first master control module 11 is specifically configured to, when the light source information is the red and green light, perform red light channel data extraction processing on the first channel data, so as to generate second red light channel data, and perform green light channel data extraction processing on the first channel data, so as to generate second green light channel data; then respectively perform remote photoplethysmography signal band-pass filtering processing on the second red light channel data and the second green light channel data, so as to generate second red light filter data and second green light filter data; and then respectively perform remote photoplethysmography signal denoise processing on the second red light filter data and the second green light filter data, so as to generate second red light signal data and second green light signal data.

For example, when the light source information is green, the first channel data consists of the red light channel data and the green light channel data, the control unit of the mobile phone, as mentioned above, performs filtering and denoise processing on the red light channel data to obtain the second red light signal data and the second green light signal data, and the finally obtained first signal data specifically consists of the second red light signal data and the second red light signal data.

In another specific implementation mode provided by the embodiment, the first master control module 11 is configured to, when the light source information is the red light, intercept the latest data segment with a duration being the display duration from the first red light signal data, so as to generate first red light display data; then perform waveform image data conversion processing on the first red light display data, so as to generate first red light waveform image data; and then send the first red light waveform image data to the display screen 14 to perform first red light waveform display processing.

Herein, the display duration is a duration with the latest waveform for display.

For example, when the display duration is 1 second, the light source information is red, the first signal data is the first red light signal data, the control unit then intercepts the latest segment of signal data with a duration being 1 second from the first red light signal data as the first red light display data, the corresponding first red light waveform image data is a display waveform with a duration being 1 second, the waveform will be displayed by the screen of the mobile phone, and herein, the color of the waveform may be set to be red during display.

In another specific implementation mode provided by the embodiment, the first master control module 11 is configured to, when the light source information is the green light, intercept the latest data segment with a duration being the display duration from the first green light signal data, so as to generate first green light display data; then perform waveform image data conversion processing on the first green light display data, so as to generate first green light waveform image data; and then send the first green light waveform image data to the display screen 14 to perform first green light waveform display processing.

For example, when the display duration is 1 second, the light source information is green, the first signal data is the first green light signal data, the control unit then intercepts the latest segment of signal data with a duration being 1 second from the first green light signal data as the first green light display data, the corresponding first green light waveform image data is a display waveform with a duration being 1 second, the waveform will be displayed by the screen of the mobile phone, and herein, the color of the waveform may be set to be green during display.

In another specific implementation mode provided by the embodiment, the first master control module 11 is configured to, when the light source information is the red and green light, intercept the latest data segment with a duration being the display duration from the second red light signal data, so as to generate second red light display data, then perform waveform image data conversion processing on the second red light display data, so as to generate second red light waveform image data; intercept the latest data segment with a duration being the display duration from the second green light signal data, so as to generate second green light display data, then perform waveform image data conversion processing on the second green light display data, so as to generate second green light waveform image data; and then send the second red light waveform image data to the display screen 14 to perform second red light waveform display processing and send the second green light waveform image data to the display screen 14 to perform second green light waveform display processing.

For example, when the display duration is 1 second, the light source information is green, the first signal data includes the second red light signal data and the second green light signal data, the control unit then respectively intercepts the latest segment of signal data with a duration being 1 second from the second red light signal data and the second green light signal data as the second red light display data and the second green light display data, and correspondingly, each of the second red light display data and the second green light display data is a display waveform with a duration being 1 second, and the two waveforms will be displayed by the screen of the mobile phone, and in order to differentiate the two waveforms, herein, the waveform of the second red light display data is set to be red and the second green light display data is set to be green during display.

The first master control module 11 is further configured to encapsulate the first signal data, the first device token information, the first device type information, and the first age information, the first gender information, the first height information and the first weight information of the test object to a first data packet according to a first protocol, and send the first data packet to the cloud server 2 by means of the first communication module 15.

Herein, the first device token information is valid device token information distributed to the first device; the first device type information is specific device type information of the first device; the first age information, the first gender information, the first height information and the first weight information are respectively age, gender, height and weight information of the test object; and the first protocol is Hyper Text Transfer Protocol (HTTP) or Hyper Text Transfer Protocol over Secure Socket Layer (HTTPS).

Herein, the first communication module 15 is specifically configured to be accessed to the Internet via a mobile communication network, a wireless local area network or a wired local area network.

The cloud server 2 includes a second master control module 21, a validity verification module 22, a parameter verification module 23, a data pre-processing module 24, an artificial intelligence blood pressure prediction module 25 and a second communication module 26.

For example, the cloud server 2 is specifically a cloud platform superposing a TENSORFLOW® frame by using a .NET kernel, the second master control module 21 is then a management unit of the cloud platform, the validity verification module 22 is a first business processing unit of the cloud platform, the parameter verification module 23 is a second business processing unit of the cloud platform, the data pre-processing module 24 is a data processing unit of the cloud platform, the artificial intelligence blood pressure prediction module 25 is a computing unit of the cloud platform, and the second communication module 26 is specifically a server communication processing unit of the cloud platform.

Herein, .NET kernel is a universal open source code development platform developed and provided by Microsoft, which may be adaptive to various processors with different architectures (such as x86 and x64 architectures of Intel and ARM32 and ARM64 architectures of ARM) and various operating systems (such as MICROSOFT WINDOWS® operating system, mAcOS® and LINUX® operating system). The TENSORFLOW® is an opensource artificial intelligence model learning frame, which is developed and provided by Google Inc., is widely applied in scenes such as graphics categorization, audio processing, recommended systems and natural language processing, and is the prevailing artificial intelligence model learning frame for the moment.

The second master control module 21 is configured to perform data analysis processing on the first data packet according to the first protocol, so as to obtain a second signal data, a second device token information, a second device type information, a second age information, a second gender information, a second height information and a second weight information.

Herein, the second signal data is equivalent to the first signal data, the second device token information is equivalent to the first device token information, the second device type information is equivalent to the first device type information, the second age information is equivalent to the first age information, the second gender information is equivalent to the first gender information; the second height information is equivalent to the first height information, and the second weight information is equivalent to the first weight information.

The validity verification module 22 is configured to perform validity verification processing on the second device token information according to a valid token list.

Herein, the valid token list is a vector table storing all valid device token information.

In another specific implementation mode provided by the embodiment, the validity verification module 22 is specifically configured to inquire the valid token list according to the second device token information, and when the second device token information satisfies the valid token list, the validity verification processing is successful.

For example, the first business processing unit obtains the valid token list from a database and then polls all valid device token information in the valid token list. When there is the second device token information in the valid token list, validity verification processing is successful.

The parameter verification module 23 is configured to, when the validity verification processing is successful, perform parameter verification processing on the second signal data, the second device type information, the second age information, the second gender information, the second height information and the second body information.

In another specific implementation mode provided by the embodiment, the parameter verification module 23 is specifically configured to examine whether none of the second signal data, the second device type information, the second age information, the second gender information, the second height information and the second weight information is null, and when none of the second signal data, the second device type information, the second age information, the second gender information, the second height information and the second weight information is null, the parameter verification processing is successful.

For example, when the second business processing unit examines that none of the second signal data, the second device type information, the second age information, the second gender information, the second height information and the second weight information is null, and one of the second signal data, the second device type information, the second age information, the second gender information, the second height information, the second weight information and the like is null, the parameter verification processing is successful.

The second master control module 21 is further configured to, when the parameter integrity verification processing is successful, perform heart rate calculation processing according to the second signal data, so as to generate heart rate data.

For example, the second signal data is signal data with a duration of 26 seconds, the management unit regards the second signal data as continuous waveform data, extracts time points of peak values of the continuous waveform data as signal time points successively, and counts an aggregate n of interval data segments within 26 seconds by taking the data segments between adjacent signal time points as the interval data segments, so as to finally obtain the heart rate data=n*60/26 (time/second).

The data pre-processing module 24 is configured to perform input data preparation processing of a blood pressure prediction module on the second signal data, the second age information, the second gender information, the second height information and the second weight information according to identifier information of the prediction module, so as to generate input data of the model.

Herein, the identifier information of the prediction module at least includes an identifier of a first convolutional neural network model and an identifier of a second convolutional neural network model. The data pre-processing module 24 includes a plurality of sub pre-processing modules.

In another specific implementation mode provided by the embodiment, the data pre-processing module 24 is specifically configured to select the corresponding first sub pre-processing module to perform input data preparation processing of the first sub blood pressure prediction module on the second signal data, the second age information, the second gender information, the second height information and the second weight information according to identifier information of the prediction module, so as to generate input data of the first model.

For example, when the identifier information of the prediction model is an identifier the first convolutional neural network model, the data processing unit then selects the first sub pre-processing module, which is specifically the pre-processing model of the first convolutional neural network model to perform input data preparation processing of the first convolutional neural network model on the second signal data, the second age information, the second gender information, the second height information and the second weight information, so as to generate input data of the first model, which is specifically the input data of the first convolutional neural network model.

For another example, when the identifier information of the prediction model is the second convolutional neural network model identifier, the data processing unit then selects the first sub pre-processing module, which is specifically the pre-processing model of the second convolutional neural network model to perform input data preparation processing of the second convolutional neural network model on the second signal data, the second age information, the second gender information, the second height information and the second weight information, so as to generate input data of the first model, which is specifically the input data of the second convolutional neural network model.

In another specific implementation mode provided by the embodiment, the first sub pre-processing module is specifically configured to baseline drift elimination processing on the second signal data, so as to generate first process signal data, then perform denoise processing on the first process signal data, so as to generate second process signal data, and then perform standard sampling and normalization processing on the second process signal data, so as to generate standard signal data; and then encapsulate the second signal data, the second age information, the second gender information, the second height information, the second weight information and the standard signal data to the input data of the first model according to a requirement on format of input data of the first sub blood pressure prediction module.

Herein, in the first sub pre-processing module, the baseline drift elimination processing may adopt processing manners such as polynomial fitting filtering, median filtering, infinite impulse response, IIR filtering, fast Fourier transform, FFT filtering or wavelet transform filtering. The denoise processing may adopt processing means such as FFT filtering, band-pass filtering or band-stop filtering. The normalization processing usually adopts a linear normalization mode. Prior to the normalization processing, it is needed to perform primary standard sampling on the signal data. The sampling frequency of the standard sampling is related to a requirement on format of the input data of the blood pressure prediction model corresponding to the pre-processing sub module.

For example, when the identifier information of the prediction model is the identifier of the first convolutional neural network model and the first sub pre-processing module is the pre-processing module of the first convolutional neural network model, the first sub pre-processing module then performs the baseline drift elimination processing on the second signal data by adopting processing manners such as polynomial fitting filtering, median filtering, IIR filtering, FFT filtering or wavelet transform filtering, so as to generate first process signal data; then perform denoise processing on the first process signal data by adopting processing manners such as FFT filtering, band-pass filtering or band-stop filtering, so as to generate second process signal data; and then perform standard sampling on the second process signal data by adopting the sampling frequency corresponding to the first convolutional neural network model and then performs normalization processing on the sampled data by the linear normalization mode, so as to generate standard signal data; and finally, then encapsulates the second signal data, the second age information, the second gender information, the second height information, the second weight information and the standard signal data to the input data of the first model, which is specifically the input data of the first convolutional neural network model according to a requirement on format of input data of the first convolutional neural network model.

For another example, when the identifier information of the prediction model is the identifier of the second convolutional neural network model and the first sub pre-processing module is the pre-processing module of the second convolutional neural network model, the first sub pre-processing module then performs the baseline drift elimination processing on the second signal data by adopting processing manners such as polynomial fitting filtering, median filtering, IIR filtering, FFT filtering or wavelet transform filtering, so as to generate first process signal data; then perform denoise processing on the first process signal data by adopting processing manners such as FFT filtering, band-pass filtering or band-stop filtering, so as to generate second process signal data; then perform standard sampling on the second process signal data by adopting the sampling frequency corresponding to the second convolutional neural network model and then performs normalization processing on the sampled data by the linear normalization mode, so as to generate standard signal data; and finally, encapsulates the second signal data, the second age information, the second gender information, the second height information, the second weight information and the standard signal data to the input data of the first model, which is specifically the input data of the second convolutional neural network model according to a requirement on format of input data of the second convolutional neural network model.

The artificial intelligence blood pressure prediction module 25 is configured to perform blood pressure prediction operation processing on the input data of the model according to the identifier information of the prediction module, so as to generate diastolic pressure data and systolic pressure data.

Herein, the artificial intelligence blood pressure prediction module 25 includes a plurality of sub blood pressure prediction modules.

Herein, the artificial intelligence blood pressure prediction module 25 at least provides two blood pressure prediction models, such as the first convolutional neural network model and the second convolutional neural network model:

(I) The first convolutional neural network model includes multiple convolutional neural network layers and a fully connected layer. Each convolutional neural network layer includes a convolutional layer and a pooling layer, where the convolutional layer is responsible for performing blood pressure characteristic extraction and calculation on the input data of the model, and the pooling layer performs downsampling on an extraction result of the convolutional layer. An output result of each convolutional neural network layer is taken as an input of the next convolutional neural network layer, and a calculated result of the final convolutional neural network layer is input into the fully connected layer for performing regressive calculation, so as to obtain the systolic pressure data and the diastolic pressure data;

(II) The second convolutional neural network model includes a two-dimensional convolutional layer, a max-pooling layer, a bath homogenization layer, an activation layer, an adding layer, a global average pooling layer, a random drop layer and a fully connected layer, where the two-dimensional convolutional layer may include a plurality of sub convolutional layers responsible for performing multiple convolutional calculation on the input data of the model. A convolutional result outputted by the two-dimensional convolutional layer includes a plurality of one-dimensional vectors. The max-pooling layer performs sampling on the convolutional result by way of taking the maximum value, so as to play a role of reducing the data volume. The bath homogenization layer performs data homogenization processing on the output result of the max-pooling layer. The activation layer performs neural network connection on the output result of the batch homogenization layer by using a nonlinear activation function. The adding layer performs weighting summation calculation on the output result of the activation layer. The global average pooling layer performs all data weighted average calculation on the output result of the adding layer. The random drop layer cuts the output result of the global average pooling layer according to randomness. Finally, the fully connected layer is used to perform two-category regressive calculation on the cut output result of the random drop layer, so as to output the diastolic pressure data and the systolic pressure data.

In another specific implementation mode provided by the embodiment, the artificial intelligence blood pressure prediction module 25 is specifically configured to select the corresponding first sub blood pressure prediction module to perform first blood pressure prediction operation processing on the input data of the first model according to the identifier information of the prediction module, so as to generate diastolic pressure data and systolic pressure data.

For example, the identifier information of the prediction model is the identifier of the first convolutional neural network model and the input data of the first model is the input data of the first convolutional neural network model, the computing unit selects the first sub blood pressure prediction model, which is the first convolutional neural network model to perform the blood pressure prediction operation processing of the first convolutional neural network model on the input data of the first convolutional neural network model, so as to generate the diastolic pressure data and the systolic pressure data.

For another example, the identifier information of the prediction model is the identifier of the second convolutional neural network model and the input data of the first model is the input data of the second convolutional neural network model, the computing unit selects the first sub blood pressure prediction model, which is the second convolutional neural network model to perform the blood pressure prediction operation processing of the second convolutional neural network model on the input data of the second convolutional neural network model, so as to generate the diastolic pressure data and the systolic pressure data.

The second master control module 21 is further configured to set state code data to be normal state code information, then constitute return data according to the heart rate data, the diastolic pressure data and the systolic pressure data, then encapsulate the return data and the state code data to a second data packet according to the first protocol, and send the second data packet to the first device by means of the second communication module 26.

In another specific implementation mode provided by the embodiment, the second communication module 26 is specifically configured to be accessed to the Internet via a mobile communication network, a wireless local area network or a wired local area network.

For example, the heart rate data is 76 time/min, the diastolic pressure data is 85 mmHg and the systolic pressure data is 112 mmHg, the management unit of the cloud platform then sets state code data to be normal state code information, sets return data consisting of the heart rate data, the diastolic pressure data and the systolic pressure data and packages the return data and the state code data according to an HTTP or HTPPS data packaging format, so as to generate the second data packet; and sends the second data packet to the mobile phone by utilizing the communication processing unit of the cloud platform.

The first master control module 11 is further configured to perform data analysis processing on the second data packet according to the first protocol, so as to obtain the return data and the state code date; acquire, when the state code data is the normal state code information, the heart rate data, the diastolic pressure data and the systolic pressure data from the return data; and then send the heart rate data, the diastolic pressure data and the systolic pressure data to the display screen 14 to perform heart rate and blood pressure data display processing.

For example, after the control unit of the mobile analyzes the second data packet, the heart rate data obtained is 76 time/min, the diastolic pressure data obtained is 85 mmHg and the systolic pressure data obtained is 112 mmHg. After receiving the data sent by the control unit, the screen of the mobile phone displays the following information: "heart rate: 76 time/min," "diastolic pressure: 85 mmHg" and "systolic pressure: 112 mmHg."

A video data based system for a blood pressure prediction provided by embodiments of the present disclosure includes a first device and a cloud server, where the first device performs video shooting on the epidermal area of the test object by using the first camera to obtain first video data, and then performs remote photoplethysmography signal conversion processing on the first video data to obtain first signal data. The cloud server then performs heart beat analysis on the first signal data to obtain heart beat data, and performs blood pressure analysis on the input data of the model integrating personalized data (information such as age, gender, height and weight) and the first signal data by using the artificial intelligence blood pressure prediction model to obtain blood pressure data (systolic pressure and diastolic pressure). Finally, the cloud server returns the analyzed data (heart beat data, systolic pressure data and diastolic pressure data) to the first device to be displayed. The first device can actuate detection in real time or monitored persistently by using the system without the test object wearing any specific collecting device, thereby reducing the implementation difficulty to detect the blood pressure of the test object in real time and monitoring the blood pressure thereof persistently and enriching the application scenes of photoplethysmography in the monitoring field.

Those skilled in the art can further realize that units and arithmetic steps in the examples described in the embodiments disclosed herein can be realized by way of electronic hardware, computer software or combination thereof. In order to describe interchangeability of hardware and software clearly, compositions and steps of the examples have been generally described in the description according to functions. Execution of these functions by way of hardware or software is dependent on a specific application and a design constraint condition of the technical scheme. Professionals can realize the described functions for each specific application by using different methods, and the implementation shall not be considered to exceed the scope of the disclosure.

Steps of the method or algorithm described in combination with embodiments disclosed herein can be implemented by way of a software module executed by hardware and process or combination thereof. The software module can be disposed in a random access memory (RAM), an internal memory, a read-only memory (ROM), an electrical programmable ROM, an electrical erasable programmable ROM, a register, a hard disc, a movable disc, a CD-ROM or any other forms of storage media known in the technical field.

The above mentioned specific embodiments have made further detailed description on purposes, technical schemes and beneficial effects of the present invention. The above mentioned is merely the preferred embodiments of the present disclosure and is not used to define the scope of protection of the present disclosure. Any modification, equivalent replacement, improvement, etc., made within the spirit and principle of the present disclosure shall be regarded as within the protection scope of the present disclosure.

What is claimed is:

1. A video data based system for a blood pressure prediction, wherein the system for predicting a blood pressure based on video data comprises a first device and a cloud server, wherein:

the first device comprises a first master control module, a first camera, a light module, a display screen and a first communication module, wherein the first master control module is a control unit of a terminal device including a processor and a memory storing executable instructions for implementing data processing and device control, the light module is a flashlight of the terminal device including light-emitting elements for irradiating an epidermal area of a test object, and the first communication module is a communication unit of the terminal device configured to access the Internet via a mobile communication network, a wireless local area network or a wired local area network;

the first master control module is configured to call the first camera and the light module to perform a video capture operation on the epidermal area of the test object for a first duration, to generate a first video data, wherein the video capture operation comprises the light module irradiating the epidermal area, the lens of the first camera aligns with and covers the epidermal area, the first camera shoots continuously for the first duration, and the first video data is generated;

the display screen is configured to receive the first video data sent by the master control module to perform display playback, wherein the display playback comprises the display screen receives the first video data sent by the first master control module and plays the first video data in real time during the video capture operation;

the first master control module is further configured to perform extraction processing of light source channel data on the first video data according to light source information to generate first channel data; then to perform remote photoplethysmography signal data conversion processing on the first channel data to generate first signal data; and then to send the first signal data to the display screen to perform signal waveform display processing according to a display duration;

the first master control module is further configured to encapsulate the first signal data, first device token information, first device type information, first age information, first gender information, first height information and first weight information of the test object to a first data packet according to a first protocol, and send the first data packet to the cloud server by means of the first communication module;

the cloud server comprises a second master control module, a validity verification module, a parameter verification module, a data pre-processing module, an artificial intelligence blood pressure prediction module and a second communication module, wherein the second master control module is a management unit of a cloud platform built with a universal open source code development platform and an opensource artificial intelligence model learning framework including a processor and a memory for implementing data analysis and task scheduling, the validity verification module is a first business processing unit of the cloud platform including a processor and a memory storing and executable instructions for validity verification, the parameter verification module is a second business processing unit of the cloud platform including a processor and a memory storing executable instructions for parameter verification, and the second communication module is a server communication processing unit of the cloud platform configured to access the Internet via a mobile communication network, a wireless local area network or a wired local area network;

the second master control module is configured to perform data analysis processing on the first data packet according to the first protocol, to obtain second signal data, second device token information, second device type information, second age information, second gender information, second height information and second weight information;

the validity verification module is configured to perform validity verification processing on the second device token information according to a valid token list;

the parameter verification module is configured to, when the validity verification processing is successful, perform parameter verification processing on the second signal data, the second device type information, the second age information, the second gender information, the second height information and the second weight information;

the second master control module is further configured to, when the parameter verification processing is successful, perform heart rate calculation processing according to the second signal data, to generate heart rate data;

the data pre-processing module is configured to perform input data preparation processing of a blood pressure prediction module on the second signal data, the second age information, the second gender information, the second height information and the second weight information according to identifier information of the prediction module, to generate input data of a model;

the artificial intelligence blood pressure prediction module is configured to perform blood pressure prediction operation processing on the input data of the model according to the identifier information of the prediction module, to generate diastolic pressure data and systolic pressure data; and the second master control module is further configured to set state code data to be normal state code information, then constitute return data according to the heart rate data, the diastolic pressure data and the systolic pressure data, then encapsulate the return data and the state code data to a second data packet according to the first protocol, and send the second data packet to the first device by means of the second communication module; and the first master control module is further configured to perform data analysis processing on the second data packet according to the first protocol, to obtain the return data and the state code data, when the state code data is the normal state code information, obtain the heart rate data, the diastolic pressure data and the systolic pressure data from the return data; and then send the heart rate data, the diastolic pressure data and the systolic pressure data to the display screen to perform heart rate and blood pressure data display processing;

wherein, the data pre-processing module comprises a plurality of sub pre-processing modules, and the artificial intelligence blood pressure prediction module comprises a plurality of sub blood pressure prediction modules;

the data pre-processing module is configured to select a corresponding first sub pre-processing module to perform input data preparation processing of a first sub blood pressure prediction module on the second signal data, the second age information, the second gender information, the second height information and the second weight information according to identifier information of the prediction module, to generate input data of a first model;

the first sub pre-processing module is configured to perform baseline drift elimination processing on the second signal data, to generate first process signal data, then perform denoise processing on the first process signal data, to generate second process signal data, and then perform standard sampling and normalization processing on the second process signal data, to generate standard signal data; and then encapsulate the second signal data, the second age information, the second gender information, the second height information, the second weight information and the standard signal data to be the input data of the first model according to a requirement for input data format of the first sub blood pressure prediction module; and the artificial intelligence blood pressure prediction module is configured to select the corresponding first sub blood pressure prediction module to perform a first blood pressure prediction operation on the input data of the first model according to the identifier information of the prediction module, to generate diastolic pressure data and systolic pressure data.

2. The system for predicting the blood pressure based on the video data of claim 1, wherein the first master control module is configured to, when the light source information is red light, perform extraction processing of red light channel data on the first video data, to generate the first channel data; when the light source information is green light, perform extraction processing of green light channel data on the first video data, to generate first channel data; when the light source information is red and green light, perform extraction processing of red light channel data on the first video data, to generate first red light channel data, perform extraction processing of green light channel data on the first video data, to generate first green light channel data, and encapsulate the first red light channel data and the first green light channel data to the first channel data.

3. The system for predicting the blood pressure based on the video data of claim 2, wherein the first master control module is configured to, when the light source information is red light, perform frame image extraction processing on the first video data, to obtain a plurality of first frame image data; count a quantity of first red pixel points with a pixel value meeting a red light pixel threshold range in each of the first frame image data, to generate a first aggregate, and perform a summation calculation on pixel values of all the first red pixel points, to generate a first pixel value sum, and then take a ratio of the first pixel value sum to the first aggregate as first frame red light channel data corresponding to each of the first frame image data; and then rank all the first frame red light channel data in a chronological order, to generate the first channel data;

the first master control module is configured to, when the light source information is green light, perform frame image extraction processing on the first video data, to obtain a plurality of second frame image data; count a quantity of first green pixel points with a pixel value meeting a green light pixel threshold range in each of the second frame image data, to generate a second aggregate, and perform a summation calculation on pixel values of all the first green pixel points, to generate a second pixel value sum, and then take a ratio of the second pixel value sum to the second aggregate as first frame green light channel data corresponding to each of the second frame image data; and then rank all the first frame green light channel data in a chronological order, to generate the first channel data; and the first master control module is configured to, when the light source information is red and green light, perform frame image extraction processing on the first video data, to obtain a plurality of third frame image data; count a quantity of second red pixel points with a pixel value meeting a red light pixel threshold range in each of the third frame image data, to generate a third aggregate, and perform a summation calculation on pixel values of all the second red pixel points, to generate a third pixel value sum, and then take a ratio of the third pixel value sum to the third aggregate as second frame red light channel data corresponding to each of the third frame image data, and then rank all the second frame red light channel data in a chronological order, to generate the first red light channel data; count a quantity of second green pixel points with a pixel value meeting a green light pixel threshold range in each of the third frame image data, to generate a fourth aggregate, and perform a summation calculation on pixel values of all the second green pixel points, to generate a fourth pixel value sum, and then take a ratio of the fourth pixel value sum to the fourth aggregate as second frame green light channel data corresponding to each of the third frame image data, and then rank all the second frame green light channel data in a chronological order, to generate the first green light channel data; and then perform multi-channel data encapsulation processing on the first red light channel data and the first green light channel data, to generate the first channel data.

4. The system for predicting the blood pressure based on the video data of claim 3, wherein the first master control module is configured to, when the light source information is the red light, perform remote photoplethysmography signal band-pass filtering processing on the first channel data, to generate first red light filter data, and perform remote photoplethysmography signal denoise processing on the first red light filter data, to generate first red light signal data;

the first master control module is configured to, when the light source information is the green light, perform remote photoplethysmography signal band-pass filtering processing on the first channel data, to generate first green light filter data, and then perform remote photoplethysmography signal denoise processing on the first green light filter data, to generate first green light signal data; and the first master control module is configured to, when the light source information is the red and green light, perform red light channel data extraction processing on the first channel data, to generate second red light channel data, and perform green light channel data extraction processing on the first channel data, to generate second green light channel data; then respectively perform remote photoplethysmography signal band-pass filtering processing on the second red light channel data and the second green light channel data, to generate second red light filter data and second green light filter data; and then respectively perform remote photoplethysmography signal denoise processing on the second red light filter data and the second green light filter data, to generate second red light signal data and second green light signal data.

5. The system for predicting the blood pressure based on the video data of claim 4, wherein the first master control module is configured to, when the light source information is the red light, intercept a latest data segment with a duration being the display duration from the first red light signal data, to generate first red light display data; then perform waveform image data conversion processing on the first red light display data, to generate first red light waveform image data; and then send the first red light waveform image data to the display screen to perform first red light waveform display processing;

the first master control module is configured to, when the light source information is the green light, intercept the latest data segment with a duration being the display duration from the first green light signal data, to generate first green light display data; then perform waveform image data conversion processing on the first green light display data, to generate first green light waveform image data; and then send the first green light waveform image data to the display screen to perform first green light waveform display processing; and the first master control module is configured to, when the light source information is the red and green light, intercept the latest data segment with a duration being the display duration from the second red light signal data, to generate second red light display data, then perform waveform image data conversion processing on the second red light display data, to generate second red light waveform image data; intercept the latest data segment with a duration being the display duration from the second green light signal data, to generate second green light display data, then perform waveform image data conversion processing on the second green light display data, to generate second green light waveform image data; and then send the second red light waveform image data to the display screen to perform second red light waveform display processing and send the second green light waveform image data to the display screen to perform second green light waveform display processing.

6. The system for predicting the blood pressure based on the video data of claim 1, wherein the first protocol comprises a Hyper Text Transfer Protocol (HTTP) and a Hyper Text Transfer Protocol over Secure Socket Layer (HTTPS);

the second signal data is equal to the first signal data, the second device token information is equal to the first device token information, the second device type information is equal to the first device type information, the second age information is equal to the first age information, the second gender information is equal to the first gender information; the second height information is equal to the first height information, and the second weight information is equal to the first weight information;

the first communication module is configured to access an Internet via a mobile communication network, a wireless local area network or a wired local area network; and the second communication module is configured to access the Internet via a mobile communication network, a wireless local area network or a wired local area network.

7. The system for predicting the blood pressure based on the video data of claim 1, wherein the validity verification module is configured to inquire the valid token list according to the second device token information, and when the second device token information satisfies the valid token list, the validity verification processing is successful.

8. The system for predicting the blood pressure based on the video data of claim 1, wherein the parameter verification module is configured to examine whether none of the second signal data, the second device type information, the second age information, the second gender information, the second height information and the second weight information is null, and when none of the second signal data, the second device type information, the second age information, the second gender information, the second height information and the second weight information is null, the parameter verification processing is successful.

* * * * *